United States Patent [19]
Kobayashi

[11] Patent Number: 4,854,692
[45] Date of Patent: Aug. 8, 1989

[54] OPHTHALMIC EXAMINATION APPARATUS

[75] Inventor: Kouji Kobayashi, Hino, Japan

[73] Assignee: Kowa Company Ltd., Japan

[21] Appl. No.: 234,809

[22] Filed: Aug. 22, 1988

[30] Foreign Application Priority Data

Aug. 31, 1987 [JP] Japan .................. 62-215028

[51] Int. Cl.⁴ .............................................. A61B 3/10
[52] U.S. Cl. .................................... 351/221; 351/206
[58] Field of Search ............... 351/206, 221, 205, 212; 250/234

[56] References Cited

U.S. PATENT DOCUMENTS 4,213,678 7/1980 Pomerantzeff et al. ............ 351/221
4,768,874 9/1988 Webb et al. ......................... 351/221
4,781,453 11/1988 Kobayashi ......................... 351/221

Primary Examiner—Rodney B. Bovernick
Assistant Examiner—P. M. Dzierzynski
Attorney, Agent, or Firm—Bruce L. Adams; Van C. Wilks

[57] ABSTRACT

Disclosed is an ophthalmic examination apparatus in which a laser beam is deflected at an eye fundus under examination to scan the eye fundus two-dimensionally, and light reflected back from the eye fundus is detected for photoelectric conversion to obtain information about the eye fundus. The apparatus includes a first optical deflector for deflecting the laser beam to scan the eye fundus in one direction and a second optical deflector for deflecting the laser beam to scan the eye fundus in a direction perpendicular to the scanning direction of the first optical deflector. A detection slit is provided which extends perpendicularly to the scanning direction of the second optical deflector and which is disposed at a position optically conjugate with the eye fundus. The reflected light is deflected in a direction parallel to the detection slit, but stationary in a direction that is perpendicular to the slit. The slit serves to remove unrequired scattered light from the optical system for examining the eye.

18 Claims, 4 Drawing Sheets

OPHTHALMIC EXAMINATION APPARATUS

BACKGROUND OF THE INVENTION

1. Field of the Invention

This invention relates to an ophthalmic examination apparatus, and more particularly to an electronic type ophthalmic examination apparatus which uses a laser beam for two-dimensional scanning of the eye fundus, collects the light reflected back from the eye fundus and subjects the light to photoelectric conversion to obtain information about the eye fundus.

2. Description of the Prior Art

Conventionally, in order to examine the eye fundus there are in wide use the method whereby the physician examines the patient's eye directly by means of an ophthalmoscope, and the method whereby a special fundus camera is used to take photographs of the eye fundus. With the advances in recent years of electronic technology, use is also being made of optoelectronic transducers such as imaging tubes and the like in place of the photographic film of the conventional fundus camera, eye fundus information being read out directly in the form of electric signals which are processed and stored in a memory or displayed on a monitor television or the like.

Of these conventional electronic examination apparatuses, one that employs laser scanning and which was developed by a U.S. ophthalmic research organization, the Retina Foundation (see U.S. Pat. No. 4,213,678 and Applied Optics, vol. 19 (1980) page 2991), has attracted attention for the many features it possesses. Specifically, by replacing the light source conventionally used in the CRT-based flying spot scanning type ophthalmic imaging system by a laser beam for eye fundus applications, restricting the incident light beam to a small zone in the center of the pupil and receiving, photoelectrically converting and amplifying the light reflected by the eye fundus from a larger area around the periphery of the pupil, it becomes possible to display on a monitor television a real-time video image of the eye fundus with a low brightness and a high S/N ratio. In addition, it becomes possible to decrease greatly the amount of fluorescent agent that is administered when fluorescent image photography of the eye fundus is to be performed. Also, by modulating the scanning laser beam it becomes possible to examine retina function in the course of observing the eye fundus image, and by utilizing the advantages of the laser beam's depth of focus, the elimination of corneal reflection by polarized light and the monochromatic nature of the light, it becomes possible to provide an excellent diagnostic apparatus.

Various improvements were subsequently made to this new type of ophthalmic apparatus by research groups in a number of countries. Particularly, the Retina Foundation announced a greatly improved ophthalmic examination apparatus (see Japanese Laid-open Patent Application No. 62(1987)-117524 and Applied Optics, vol. 26 (1987) page 1492). Specifically, with this apparatus, in addition to two-dimensional scanning of the eye fundus by the incident laser beam, by also two-dimensionally scanning light reflecting from the fundus and using an optoelectronic detector with an extremely small aperture to detect the reflected light, it becomes possible to provide a marked improvement in the contrast of the eye fundus image thus obtained. In other words, by constituting the entire optical system of reflective-type elements (i.e. mirrors) and scanning both the incident and reflected light beams simultaneously (double-scanning), fixing the scanning of the reflected light acquired by the optoelectronic light detector and detecting only reflected light from a point that is optically conjugate with the fundus of the eye being examined, it became possible to exclude entirely the effect of unrequired light scattered by the optical system of the eye. The apparatus achieved a high level of perfection for clinical ophthalmic examination purposes by enabling retinal blood vessel information to be acquired with sufficient contrast using red light, whereas conventionally green light was required to extract such information, it being considered impossible to obtain an improvement in retinal blood vessel contrast using light with red or longer wavelength; and enabling fundus images of adequate quality for diagnostic purposes to be obtained without the use of an agent to dilate the pupil, i.e. with the pupil in the contracted state to some extent.

The major drawback with this type of apparatus is that the system for controlling the laser beam deflection is difficult. In the reference material cited above (U.S. Pat. No. 4,213,678 and Applied Optics, vol. 19 (1980) page 2991), two mechanical laser beam deflection systems (two sets of oscillating mirrors or galvanometer mirrors) are employed which are operated at a horizontal scanning frequency of 7.8 KHz and a vertical scanning frequency of 60 Hz. But there is the problem that bearings of the horizontal scanning mirror wear severely and its durability is poor because of its high scanning frequency of 7.8 KHz. Moreover, in order to obtain high-definition video images it is necessary to use higher laser beam horizontal scanning frequencies.

For this, in later reference materials (Japanese Laid-open Patent Application No. 62(1987)-117524 and Applied Optics, vol. 26 (1987) page 1492), use is made of a multi-facet mirror for the horizontal optical deflector, driven at a scanning frequency of 15.75 KHz (an oscillating mirror driven at 60 Hz is used for vertical scanning). This scanning frequency is the same as that based on the standard NTSC system raster scan, and is an extremely apt choice in terms of the current state of imaging electronics. It is also very practical with respect to interfacing with peripheral equipment. However, there are many problems in realizing a scanning frequency of 15.75 KHz, as it means a mirror with, for example, 25 faces would have to rotate at 37,800 rpm.

First and foremost are problems relating to service life and durability. Such problems are common to this type of high-mechanically-operated optical deflector including the above-mentioned oscillating mirrors. Even in a high-speed rotationary system using pneumatic bearings, the bearings wear after several thousand starts and stops or metal fatigue leads to a degradation in precision, shortening the system's service life. Secondly, there are the problems of shaft movement, facet inclination and facet division tolerance(facet-to-facet errors). With a multi-facet rotating mirror, wobbling or jitters in shaft play, mirror inclination and mirror division angle errors can produce unevenness of the laser beam raster, and the system is also prone to be influenced by external vibration.

The third point relates to making the system smaller. An apparatus employing a high-speed multi-facet rotating mirror requires large bearings, and because the rotation is limited to a predetermined direction, it is very difficult to reduce the size of the system.

In a mechanical type multi-facet rotating mirror system, the reflective-type deflector is advantageous for simultaneously scanning of the incident beam and the reflected light (double-scanning), and it helps to improve the contrast of the image that is obtained. As stated above, however, there are many problem points relating to the performance of the deflector itself. Also, while in an apparatus that performs double-scanning using reflector-type deflectors there is a major advantage in constituting the entire optical system of reflective elements (mirrors), attempting to introduce an additional refractive optical system can lead to problems. Introducing an additional set of lenses, for example, to change the angle of view can lead to harmful light effects produced by reflection from the lens surfaces. However, such problems can be reduced by choosing an appropriate stop or surface angle. As such, these may be relatively small problems compared with problems arising from the characteristics of the overall apparatus or the deflector. However, in this type of apparatus, in terms of the utility of the apparatus it is extremely important to be able, swiftly and fully, to change the angle of view which establishes the imaging range of the eye fundus that is being examined.

If in the near future there should appear high-definition television, which aims to improve picture resolution and quality, the horizontal scanning frequency will be around 33 KHz. Adapting a mechanical system of deflection to such a high scanning frequency would become even more difficult, owing the problems cited above.

The practical application was then tried of an idea that was announced which involved the use for the horizontal deflector of a non-mechanical acousto-optical device having no moving parts. However, because the acousto-optical device is basically a transmission-type deflector that utilizes diffraction and resolution is limited by the size of the device's aperture and the angle of deflection, it is not conducive to improving the contrast of an image that is obtained using double-scanning of the incident beam and the reflected light. That is, with the optical system of the conventional ophthalmic examination apparatus employing an acousto-optical deflector, unrequired light scattered by parts of the eye-ball other than the fundus could not be excluded, and when the mydriasis was insufficient, there was a problem of deterioration in the contrast of the resulting fundus image.

FIG. 4 shows the optical system of a conventional ophthalmic examination apparatus using an acousto-optical deflector (AOD). See, for example, Japanese Patent Application No. 61(1986)-106688. A laser beam 101 from the laser light source is deflected in one dimension (horizontally) by its passage through the AOD 102. Bracketing the AOD 102 are lenses 103 and 104 to shape the laser beam for impingement on the rectangular aperture of the AOD and to return the beam emerging from the AOD to its original shape. The laser beam scanned by means of the AOD passes through a lens 105, a slit 106 and a lens 107 to a mirror 108. The slit 106 blocks zero-order light and transmits only first-order light. Attached to a galvanometer 109 is a mirror 108 which is oscillated to effect deflection (scanning) in a direction (vertical) that is at right-angles to the direction in which the laser beam is deflected by the AOD. The laser beam scanned two-dimensionally by the mirror 108 passes through a lens 110, is reflected by a mirror 111 and is projected onto the fundus of the eye under examination 113 by an objective lens 112. The light reflected by the fundus goes through the objective lens 112, passes the periphery of the mirror 111 and via a lens 114 is concentrated on the light receiving face of a light-receiving element 115 and undergoes photoelectric conversion. Disposed on the front of the light-receiving element 115 is a filter 116 which filters light of the laser-beam wavelength.

As is apparent from FIG. 4, the light-receiving element 115 receives the major portion of the light emerging from the pupil of the eye being examined 113. As well as the light directly reflected by the fundus, it also detects almost all of the unrequired scattered light from the optical system of the eyeball. Particularly when the pupil is small, this unrequired scattered light causes a deterioration in the contrast of the obtained fundus image. However, with the kind of optical system shown in FIG. 4, because, with respect to the light reflected by the fundus, the light is always deflected two-dimensionally at a point that is optically conjugate with the eye fundus, it has been impossible to detect just the directly reflected light component from the fundus, separately from the unrequired scattered light component.

SUMMARY OF THE INVENTION

Therefore, the purpose of this invention is to provide a new type of practical laser-scanning ophthalmic examination apparatus which is highly reliable and offers excellent operability and performance, wherein reliable deflection control at a high scanning frequency can be realized from horizontal scanning of a laser beam without using a mechanical deflector.

It is another object of an invention to provide an ophthalmic examination apparatus in which the optical system of the apparatus including the deflector can be made small.

It is still another object of an invention to provide an ophthalmic examination apparatus in which the angle of view can be changed easily and, moreover, the effect of unrequired scattered light can be excluded to obtain an eye fundus image having sufficiently improved contrast.

The present invention provides an ophthalmic examination apparatus in which a laser beam is deflected at an eye fundus under examination to scan the eye fundus two-dimensionally, and light reflected back from the eye fundus is detected for photoelectric conversion to obtain information about the eye fundus. The apparatus comprises a laser light source for producing the laser beam of a single or plurality of wavelength; a first non-mechanical optical deflector for deflecting the laser beam to scan the eye fundus in one direction at a predetermined frequency; a second mechanical optical deflector for deflecting the laser beam to scan the eye fundus in a direction perpendicular to the scanning direction of the first optical deflector at a frequency that is lower than the frequency of the first optical deflector; a detection slit having an aperture which extends perpendicularly to the scanning direction of the second optical deflector and which is disposed at a position optically conjugate or substantially conjugate with the eye fundus under examination; optical means for deflecting light reflected from the eye fundus relative to the scanning direction of the second optical deflector in such a manner that the reflected light is deflected in a direction parallel to the detection slit, but stationary in a direction that is perpendicular to the slit; and light receiving elements for detecting light passing through the detection slit which serves to remove unrequired scattered light from the optical system for examining the eye to obtain the eye fundus information.

In one preferred embodiment of the present invention, an ophthalmic examination apparatus comprises a laser light source for producing the laser beam of a single or plurality of wavelength; a first non-mechanical optical deflector for deflecting the laser beam to scan the eye fundus in one direction at a predetermined frequency; a first optical system including the first optical deflector for deflecting the laser beam to scan the eye fundus one-dimensionally about a pivot of deflection existing at a position that is optically conjugate or substantially conjugate with the pupil of the eye being examined; a second mechanical optical deflector for deflecting the laser beam to scan the eye fundus in a direction perpendicular to the scanning direction of the first optical deflector at a frequency that is lower than the frequency of the first optical deflector; a second optical system including the second optical deflector for directing the laser beam deflected by the first and second optical deflectors towards the eye fundus and for receiving light reflected from the eye fundus, the second optical system being capable of passing one- and two-dimensionally deflected light; a detection slit having an aperture which extends perpendicularly to the scanning direction of the second optical deflector and which is disposed at a position optically conjugate or substantially conjugate with the eye fundus under examination; light receiving elements for receiving the light reflected from the eye fundus; and a third optical system including the detection slit for directing towards the light receiving elements the reflected light from the eye fundus that has been separated from the incident laser beam and deflected one-dimensionally in a direction parallel to the detection slit.

In another embodiment of the present invention, an ophthalmic examination apparatus comprises a laser light source for producing the laser beam of a single or plurality of wavelength; a first non-mechanical optical deflector for deflecting the laser beam to scan the eye fundus in one direction at a predetermined frequency; an optical system capable of changing the range of angles of deflection of the one-dimensionally deflected laser beam independently of the angle of deflection of the first optical deflector; a second mechanical optical deflector for deflecting the laser beam to scan the eye fundus in a direction perpendicular to the scanning direction of the first optical deflector at a frequency that is lower than the frequency of the first optical deflector; and an electronic control means for varying the range of the angles of deflection of the laser beam deflected by the second optical deflector, so that the range of angles of view of the eye fundus can be varied.

According to the present invention, the optical system of the apparatus including the deflector can be made compact and reliable deflection control at a high scanning frequency can be realized by using a nonmechanical deflector for horizontally scanning the laser beam. In addition, the effect of unrequired scattered light can be excluded by means of a detection slit and peripheral optical system components, making it possible to obtain an eye fundus image having sufficiently improved contrast, while it also becomes possible to use a photomultiplier with a small aperture as the light-receiving element and to improve the S/N ratio of the image signal. Moreover, the reduced size of the light-receiving element helps reduce the size of the apparatus. Also, by combining optical changing of the angle of view relative to the horizontal direction with changing of the angle of view relative to the vertical by means of electronic control means, there is no harmful light resulting from angle-of-view change lenses and it becomes possible easily to change the range of viewing angles of the eye fundus imaging, i.e., the resolution of the resultant image can be changed, enabling a new, practical laser-scanning ophthalmic examination apparatus to be realized which offers a high degree of overall superiority in reliability, operability and performance.

BRIEF DESCRIPTION OF DRAWINGS

The objects and features of the present invention will become more apparent from a consideration of the following detailed description taken in conjunction with the accompanying drawings in which.

DETAILED DESCRIPTION OF THE PREFERRED EMBODIMENTS

The embodiments of the present invention will now be described in the following with reference to FIGS. 1 to 3.

Figure 1:
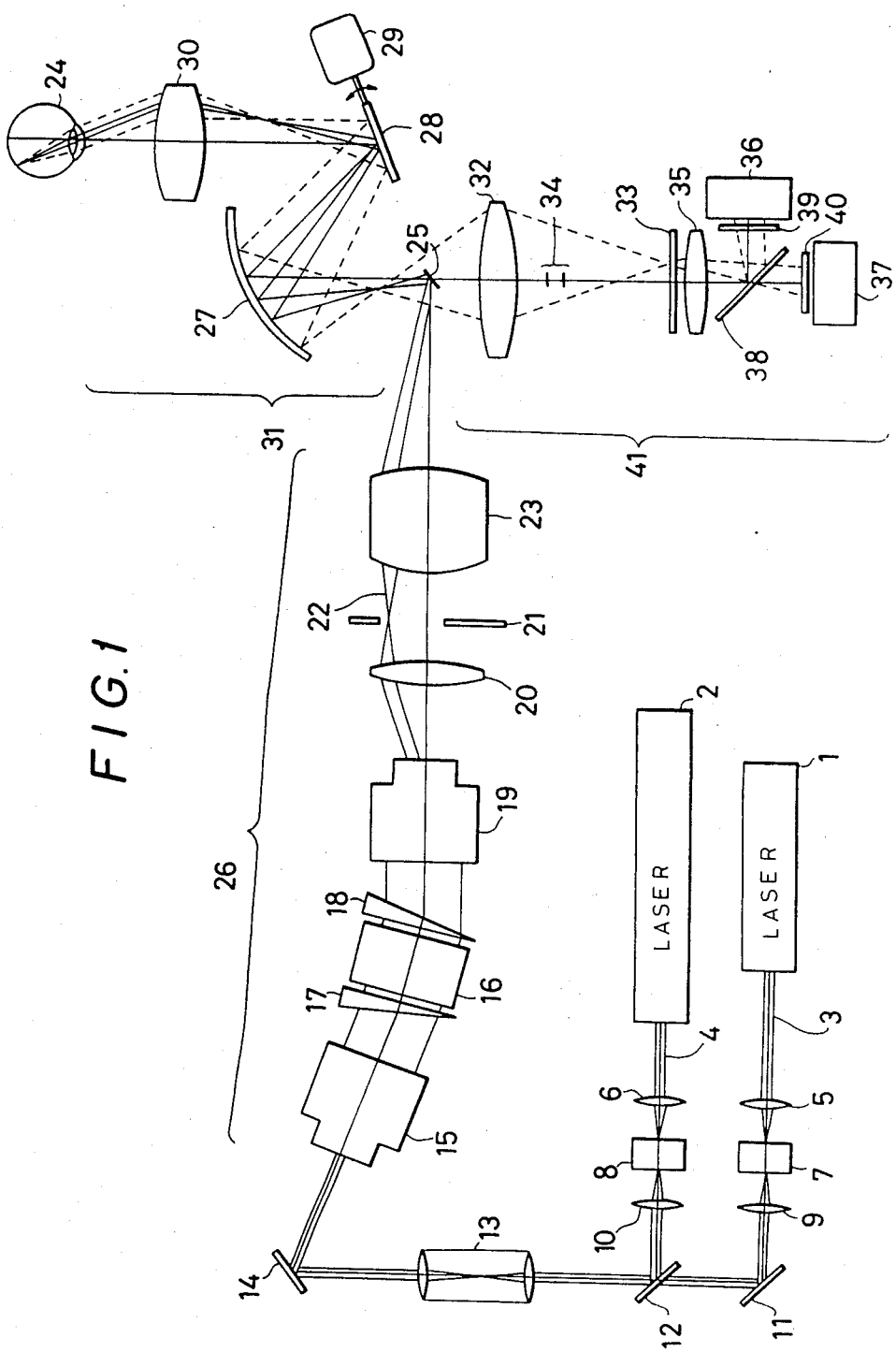
FIG. 1 is a schematic illustration of the overall configuration of the optical system of the apparatus according to the present invention.

FIG. 1 is a general schematic of the optical system arrangement of the ophthalmic examination apparatus according to the present invention. In FIG. 1, reference numerals 1 and 2 denote laser light sources of helium-neon (He-Ne) or argon ($Ar^+$), for example. The wavelength of the light produced by the He-Ne laser light source is, for example 632.8 nm (red), 611.9 nm (orange), 594.1 nm (yellow) or 543.5 nm (green). The wavelength of the light produced by the $Ar^+$ laser light source is, for example, 514.5 nm (blue-green) or 488 nm (blue).

The respective laser beams 3 and 4 from the laser light sources are condensed by lenses 5 and 6 respectively and impinge on acousto-optic modulators (hereinafter referred to as "AOM") 7 and 8. The AOMs are for intensity modulation purposes, and when gas lasers are employed as the light source can be used for stabilization of the laser beam intensity and for intensity modulation of the laser beam by means of video signals, producing a target to fix the line of sight of the person being examined, and also for the production of arbitrary index for examination of retinal function. The light beams emitted by the AOMs pass through respective lens 9 and 10 and are reflected by mirrors 11 and 12. Mirror 12 is a dichroic mirror that transmits the laser beam from the laser light source 1 and reflects the beam from the laser-light source 2, thereby forming a composite beam of two different wavelengths.

After the dichroic laser beam formed by the mirror 12 has been expanded to a specific size by a beam expander 13, the beam is deflected by a mirror 14 and impinges on a lens 15. The lens 15 is for shaping the laser beam for the rectangular aperture of the following acousto-optic deflector (hereinafter referred to as AOD) 16, and incorporates a multiplicity of cylindrical lenses. The AOD 16 is bracketed by a pair of prisms 17 and 18 for compensating for the wavelength dependency of the angle of incidence and angle of emergence of the laser beam with respect to the AOD. The laser beam deflected in one dimension (horizontally) by the AOD is reformed from the rectangular(elliptical) shape to its original circular shape by a lens 19 which is constituted analogously to the lens 15, following which the beam passes through a lens 20 and a slit 21. The slit 21 is for blocking zero-order light (not shown) from the AOD 16 and using only first-order diffraction light. The first-order diffraction light 22 from the slit 21, passing through a lens 23, is scanned one-dimensionally with the center portion of a mirror 25 disposed at a position optically conjugate with the pupil of the eye being examined 24 as the pivot point of deflection. For convenience, the optical system for one-dimensional scanning of the laser beam constituted of the components from lens 15 to lens 23, including the AOD 16, and denoted by reference numeral 26, will hereinafter be referred to as the first optical system.

For the AOD 16, a laser beam scanning frequency of 15.75 KHz is practically corresponding to the ordinary NTSC standard television horizontal scan rate. However, to adapt the system to the forthcoming high-definition television, a frequency of 33 KHz is possible. Also, the AOD deflection angle is proportional to the wavelength of the light, i.e., the angle of deflection varies according to the wavelengths of the scanning laser beams. In this embodiment the same deflection angle ranges for each wavelength are utilized.

The laser beam reflected by the mirror x25 is reflected by a concave mirror 27, which acts like a lens, onto a mirror 28. The mirror 28 is attached to a galvanometer 29 and is for the vertical scanning of the laser beam. The mirror 28 is referred to as an oscillating mirror or as a galvanometer mirror. The laser beam scanned two-dimensionally by the mirror 28 is passed through an objective lens 30 and is thereby projected onto the eye fundus via the central portion of the pupil of the eye being examined 24. The reflected light from the fundus, which is represented by the dashed line in FIG. 1, is guided via the objective lens 30 to be reflected by the mirror 28 and again reflected by the concave mirror 27. The light reflected from the eye fundus is in a two-dimensionally scanned state, but after being reflected by the mirror 28 and guided to the concave mirror 27 it is fixed in a vertical scanning state by the deflective action of the mirror 28; i.e., it becomes reflected light that is scanned only one-dimensionally. The concave mirror 27, oscillating mirror 28 and objective lens 30 are used for both the light that is projected onto the eye fundus and light reflected from the fundus. On the objective lens side of the oscillating mirror, the scanning light exists in a two-dimensional state, while on the concave mirror side thereof it exists in a one-dimensional state; in this invention this portion is referred to as the second optical system and is denoted by reference numeral 31.

A vertical scanning frequency of 60 Hz corresponding to the ordinary television vertical scanning frequency was chosen for the oscillating mirror 28. Unlike in the case of the AOD described above, with respect to vertical scanning, the angle of deflection of the oscillating mirror is not dependent on the wavelength of the light, but remains substantially identical.

Light reflected from the eye fundus and then reflected by the concave mirror 27 passes around the periphery of the mirror 25, and is separated from the projected laser light. This one-dimensionally scanned reflected light from the fundus that passes around the periphery of the mirror 25 passes through a lens 32 and is concentrated on a detection slit 33. The width of the detection slit 33 is narrow and one-dimensionally extending, being on the order of 100 μm, and it is disposed at a point that is optically conjugate or substantially optically conjugate with the fundus of the eye 24. The function of the detection slit is to transmit only light directly reflected from the fundus and block the major portion of unrequired scattered light components, such as for example multiple scattered light in the eye fundus or light scattered by the crystalline lens or vitreous bodies. Between the lens 32 and the detection slit 33 is a black spot 34 for eliminating the effect of reflected light from the surface of the objective lens 30. Reflected light from the eye fundus passing through the detection slit 33 is projected onto the light-receiving surfaces of light-receiving elements 36 and 37, which are for example photomultipliers or the like. The light-receiving elements 36 and 37 correspond to the two wavelengths of the scanning laser beams, and detect the respective wavelengths separated by the dichroic mirror 38. Disposed in front of the light-receiving elements 36 and 37 are filters 39 and 40 respectively which correspond to the wavelengths of the laser beams. In this invention, a third optical system (denoted by reference numeral 41) is constituted of the components from the lens 32 to the light-receiving elements 36 and 37, including the detection slit 33, and guides the one-dimensionally scanned light that is separated from the projected laser light.

Among the merits of this type of optical system are the exclusion of unrequired scattered light by the detection slit 33, and the ability to vertically compress the light beams reflected from the eye fundus on the light-receiving faces of the light-receiving elements 36 and 37. That is, as the light-receiving elements there can be used photomultipliers having a small (rectangular) aperture and possessing a high quantum efficiency, which provide advantages such as a better image signal S/N ratio and the ability to decrease the size of the apparatus owing to the smaller size of the light-receiving elements.

Figure 2:
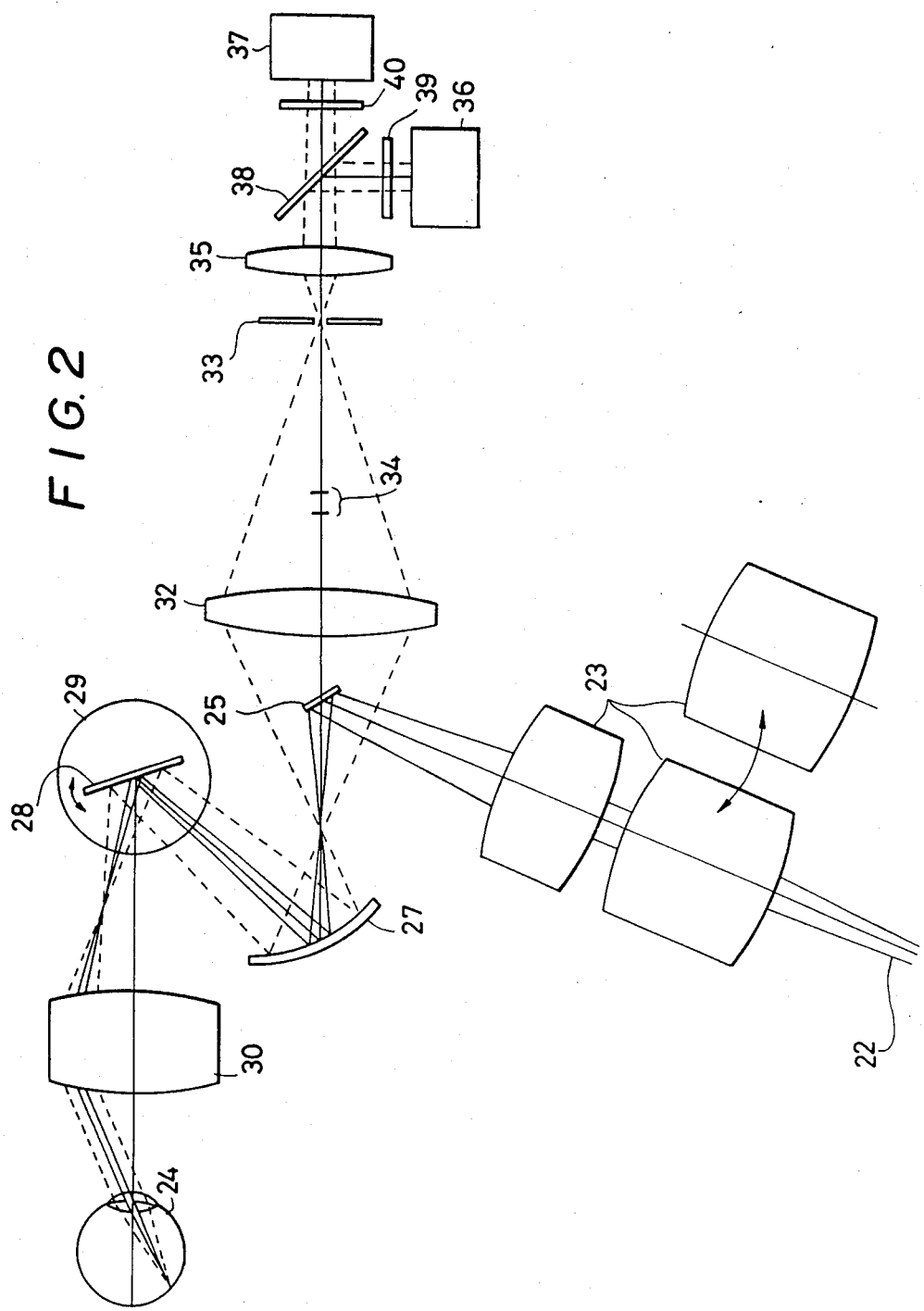
FIG. 2 is a schematic illustration mainly of the components of the light-receiving section shown in FIG. 1.

FIG. 2 illustrates part of the above first optical system 26 as well as the second and third optical systems 31 and 41 in a configuration that reproduces the one used more closely than the depiction of FIG. 1. In FIG. 2, the laser beam 22 deflected one-dimensionally (in the horizontal direction) by the AOD (first-order diffraction light) is guided via the lens 23 to be scanned with the mirror 25 as the pivot point of deflection, said mirror 25 being disposed at a position that is optically conjugate with the pupil of the eye being examined.

In FIG. 2 the scanning direction of first-order diffraction light 22 is perpendicular to the drawing sheet so the laser beam is therefore depicted as following the central axis of the optical system. While not described with reference to FIG. 1, lens 23 is constituted of a multiplicity of lenses and has the functions of changing the viewing angle and adjusting the focal point. The laser beam reflected by the mirror 25 and scanned in the horizontal direction (vertically with reference to the FIG. 2 drawing sheet) is reflected by the concave mirror 27, is again reflected by the oscillating mirror 28 attached to the galvanometer 29 and is also scanned vertically (horizontally with respect to the drawing sheet). The laser beam scanned two-dimensionally (horizontally and vertically) by the oscillating mirror 28 is projected onto the fundus of the eye 24 by the objective lens 30, and the light reflected from the eye fundus, depicted by a dotted line in FIG. 2, is returned through the same optical systems 30, 28 and 27 as the incident beam.

The light reflected from the eye fundus separated from the incident beam by the mirror 25 portion passes through the lens 32, the detection slit 33, the lens 35, the mirror 38 and the filters 39 and 40 to the light-receiving elements 36 and 37, where it is subjected to opto-electronic conversion to obtain an image signal. With reference to FIG. 2, the reflected light from the eye fundus, represented by the dotted lines from the oscillating mirror 28 to the light-receiving elements 36 and 37 is in a state of horizontal scanning only (vertical with reference to the FIG. 2 drawing sheet). Therefore the laser beam is depicted as following the central axis of the optical system as if it is in a non-scanning state. As is apparent from the drawing, the detection slit 33 is disposed at a position that is optically conjugate with the fundus of the eye 24 and plays a major role with respect to eliminating unrequired scattered light from the optical system of the eyeball.

As mentioned above, lens 23 is constituted of a multiplicity of lenses and has the functions of changing the angle of view and adjustment of the focal point. For example, the scanning range of the laser beam can be altered by changing some of the lenses, and the range of the angle of view with respect to the imaged eye fundus can be changed. However, as can be seen from FIG. 2, changing the angle of view by means of the lens 23 can only be done in a one-dimensional direction, i.e. horizontally (vertically with respect to the drawing sheet of FIG. 2). Therefore, with this invention, by simultaneously changing the range of the angle of deflection of the oscillating mirror 28 by electronic control means, the angle of view in the vertical direction (horizontally with respect to the FIG. 2 drawing sheet) can be changed for two-dimensional changing of the angle of view. Changing the angle of view in the horizontal direction by the lens 23 in combination with changes in the vertical direction by means of the oscillating mirror 28 provides superior results. Specifically, if the lens-based two-dimensional change of viewing angle as effected with the conventional type of fundus camera is applied to the optical system of the present invention, the lens for changing the angle of view has to be located between the oscillating mirror 28 and the eye being examined 24. In this case, because an angle-of-view change lens having a multiplicity of lens surfaces is located along the same optical path as that used for the incident beam going to the fundus and the light reflected therefrom, the harmful light reflecting from the lenses' surface will all be picked up by the light-receiving elements 36 and 37. Or, the number of black spots 34 shown in FIG. 2 will have to be increased, allowing the undesirable sacrifice of the S/N ratio of the detected signals.

With this type of angle-of-view change function, the diameter of the laser beam impinging on the mirror 28 and on the pupil of the eye being examined 24 can be varied, and as such the resolution of the obtained image can be varied. If for example the viewing angle is changed from a wide to a narrow angle, such as from 40° to 30° to 20°, the diameter of the spot of laser light on the eye fundus becomes smaller, raising the resolution of the image.

It is also possible to provide the lens 23 with focal point and diopter adjustment capabilities, with respect to the eye fundus. Such capabilities are important, should the eye being examined exhibit a marked refractive abnormality. With reference to FIG. 2, this type of adjustment means a displacement in the locations that are optically conjugate with the fundus of the eye. Therefore it is rational for the detection slit 33, that is located at a position that is optically conjugate with the eye fundus, to be made movable for focal point adjustment.

Figure 3:
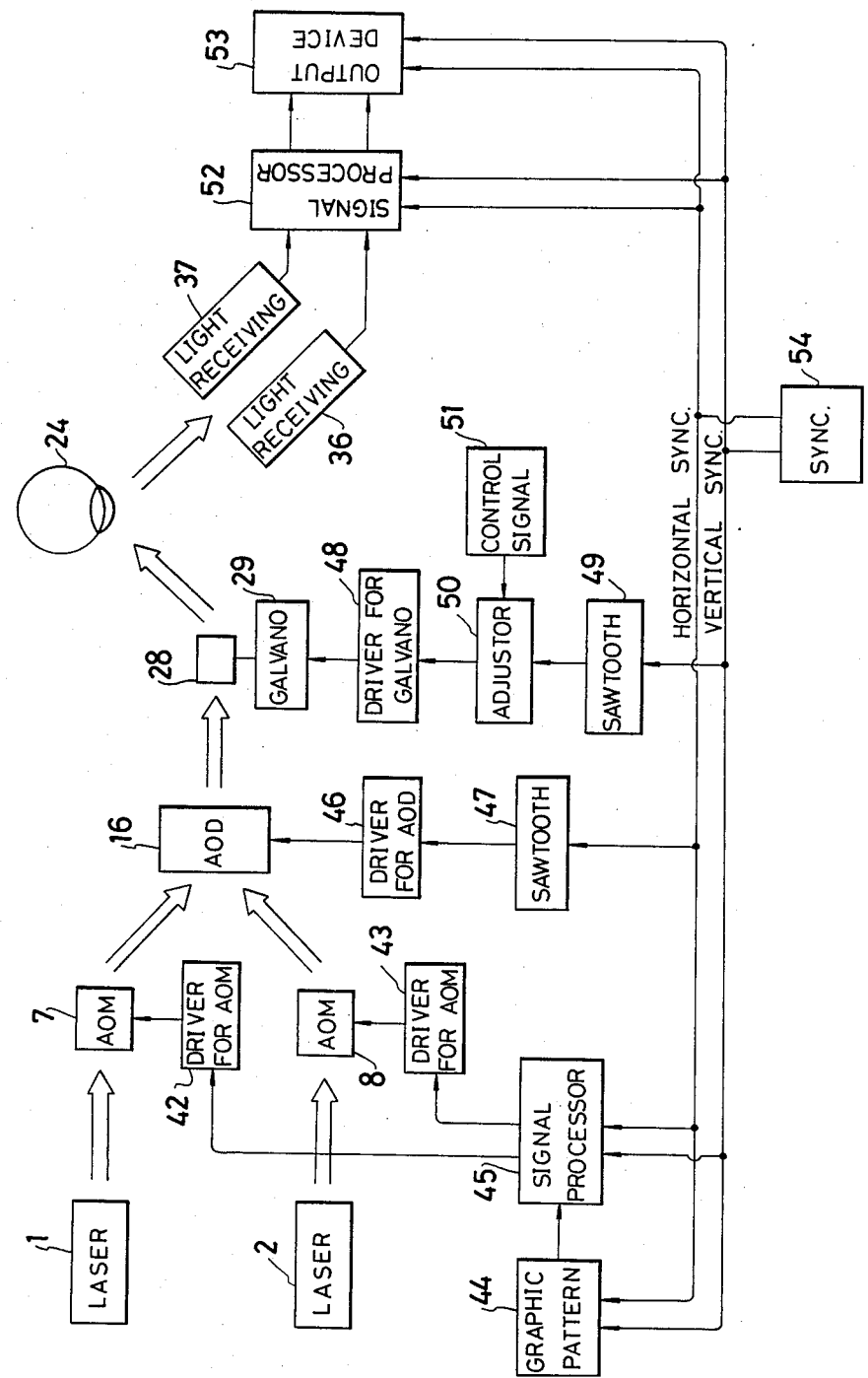
FIG. 3 is a block diagram showing the electrical configuration of the apparatus of FIG. 1.
Figure 4:
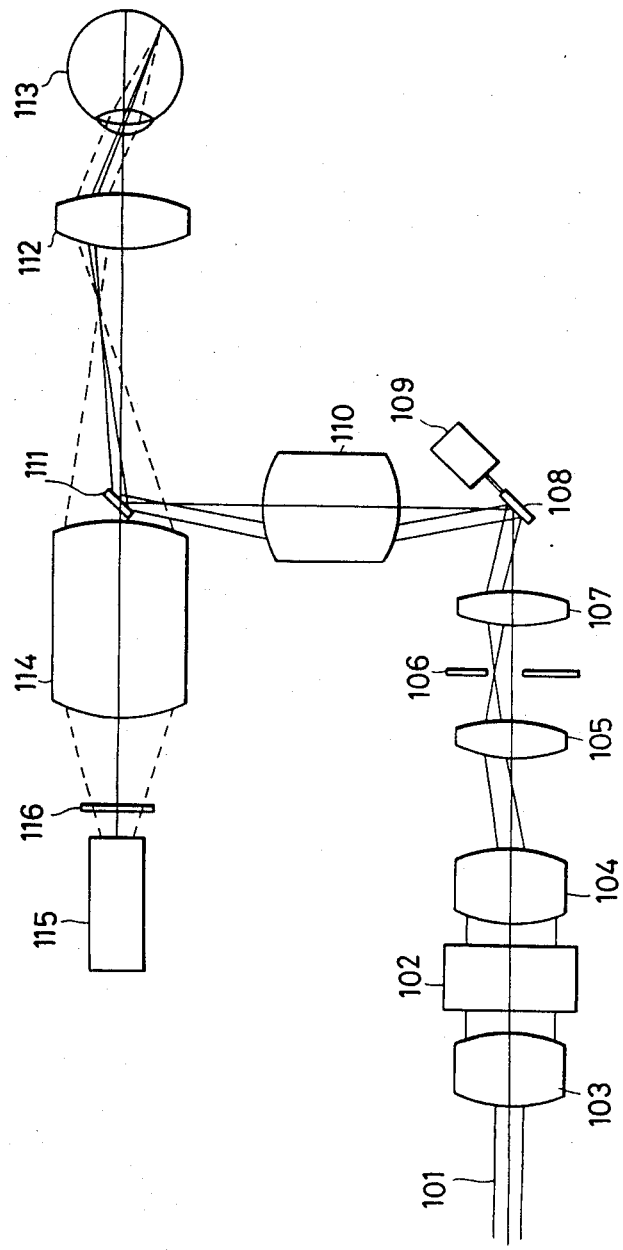
FIG. 4 is a schematic illustration of the arrangement of a conventional apparatus.

FIG. 3 is a block diagram illustrating the electrical configuration of the ophthalmic examination apparatus according to the present invention. The laser beams produced by the laser light sources 1 and 2 are intensity-modulated by the AOMs 7 and 8, and after the beams are deflected horizontally and vertically by means of the AOD 16 and the oscillating mirror 28, they are beamed at the eye being examined 24. Connected to the AOMs 7 and 8 are corresponding drivers 42 and 43. Applied to the drivers 42 and 43 is a video signal generated by a graphic pattern generator 44 and processed by a signal processor 45. The graphic pattern generator is for producing various patterns of video signals such as Landolt rings, for example, and other such indexes for fixing the person's line of vision and examining retinal function and the like. A driver 46 is connected to the AOD 16, the driver 46 being controlled by a sawtooth signal generated by a sawtooth waveform generator 47. Connected to the galvanometer 29 which drives the mirror 28 is a driver 48 which is controlled by a sawtooth signal generated by a sawtooth waveform generator 49 and processed by a magnification/offset adjuster 50. The magnification/offset adjuster 50 is for adjusting the d.c. potential and the size of the sawtooth wave in accordance with a control signal from a control signal generator 51, for changing the range of the laser beam deflection angle by means of the oscillating mirror 28. When the viewing angle is to be changed, the horizontal viewing angle is changed optically by means of the lens 23 (FIGS. 1 and 2). By simultaneously changing the vertical angle of view by electronically changing the deflection angle range of the oscillating mirror, two-dimensional change can be effected. In accordance with the signal from, for example, a sensor (not shown) provided in the optical system, the control signal generator 51 will generate a control signal for driving the magnification/offset adjuster to change the deflection angle of the oscillating in an interlocking arrangement with the adjustment of the lens 23.

The light reflected by the eye fundus is converted to electrical signals by the light-receiving elements 36 and 37, and after processing by a signal processor 52 are sent to an output device 53 such as a monitor TV or image processor in the form of fundus image video signals. The deflection of the laser beams and the modulation control system are synchronized with the signal processing and output systems on the light receiving side by means of horizontal and vertical synchronization signals generated by a synchronization signal generator 54, enabling time-wise control of the overall system.

As mentioned in the above, with the horizontal deflector AOD 16, the angle of deflection is wavelength-dependent. Therefore, if laser beams having a multiplicity of wavelengths are scanned simultaneously using a single AOD, color dispersion occurs. With a He-Ne laser light source 1 having a wavelength of 632.8 nm (red) and an Ar$^+$ laser light source 2 having a wavelength of 514.5 nm (blue-green), for example, using the AOD to scan simultaneously these beams of two wavelengths and picking up the light reflected from the eye fundus by means of light-receiving elements 36 and 37, the video signal thus derived will be affected by color dispersion. Therefore, to eliminate the effects of color dispersion use is made of the electronic signal processing means disclosed by the present inventor in Japanese Patent Application No. 61(1986)-080236. That is the purpose of the signal processor 52 shown in FIG. 3. Also, if in order to check visual function the laser beams having two wavelengths are modulated by AOMs 7 and 8 and AOD 16 is used to simultaneously scan them on the eye fundus, the pattern described by the laser beam rasters, as seen by the subject will be affected by color dispersion. The effects of this color dispersion can be eliminated by means of the electronic signal processing means disclosed by the present inventor in Japanese Patent Application No. 61(1986)-080237. That is the purpose of the signal processor 45 in FIG. 3. For details refer to the specifications of the said patent application.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed:

1. An ophthalmic examination apparatus in which a laser beam is deflected at an eye fundus under examination to scan said eye fundus two-dimensionally, and light reflected back from said eye fundus is detected for photoelectric conversion to obtain information about the eye fundus, said apparatus comprising:
    a laser light source for producing said laser beam of a single or plurality of wavelength;
    a first non-mechanical optical deflector for deflecting said laser beam to scan said eye fundus in one direction at a predetermined frequency;
    a second mechanical optical deflector for deflecting said laser beam to scan said eye fundus in a direction perpendicular to the scanning direction of said first optical deflector at a frequency that is lower than the frequency of said first optical deflector;
    a detection slit having an aperture which extends perpendicularly to the scanning direction of said second optical deflector and which is disposed at a position optically conjugate or substantially conjugate with said eye fundus under examination;
    optical means for deflecting light reflected from said eye fundus relative to the scanning direction of said second optical deflector in such a manner that the reflected light is deflected in a direction parallel to the detection slit, but stationary in a direction that is perpendicular to the slit; and
    light receiving elements for detecting light passing through said detection slit which serves to remove unrequired scattered light from the optical system for examining the eye to obtain said eye fundus information.

2. An ophthalmic examination apparatus according to claim 1, wherein said first optical deflector is an acousto-optical device.

3. An ophthalmic examination apparatus according to claim 1, wherein said second optical deflector is an oscillating mirror.

4. An ophthalmic examination apparatus according to claim 1, wherein said optical means includes said second optical deflector.

5. An ophthalmic examination apparatus according to claim 1, wherein a range of laser beam deflection angles can be varied to vary an angle of view of an eye fundus being examined independently of a deflection angle of said first optical deflector.

6. An ophthalmic examination apparatus according to claim 5, wherein the range of angles of laser beam deflection produced by the second optical deflector can be varied in accordance with the variation in said laser beam deflection angle.

7. An ophthalmic examination apparatus in which a laser beam is deflected at an eye fundus under examination to scan said eye fundus two-dimensionally, and light reflected back from said eye fundus is detected for photoelectric conversion to obtain information about the eye fundus, said apparatus comprising:
    a laser light source for producing said laser beam of a single or plurality of wavelength;
    a first non-mechanical optical deflector for deflecting said laser beam to scan said eye fundus in one direction at a predetermined frequency;
    a first optical system including said first optical deflector for deflecting said laser beam to scan said eye fundus one-dimensionally about a pivot of deflection existing at a position that is optically conjugate or substantially conjugate with the pupil of the eye being examined;
    a second mechanical optical deflector for deflecting said laser beam to scan said eye fundus in a direction perpendicular to the scanning direction of said first optical deflector at a frequency that is lower than the frequency of said first optical deflector;
    a second optical system including said second optical deflector for directing said laser beam deflected by said first and second optical deflectors towards said eye fundus and for receiving light reflected from the eye fundus, said second optical system being capable of passing one-and two-dimensionally deflected light;
    a detection slit having an aperture which extends perpendicularly to the scanning direction of said second optical deflector and which is disposed at a position optically conjugate or substantially conjugate with said eye fundus under examination;
    light receiving elements for receiving said light reflected from the eye fundus; and
    a third optical system including said detection slit for directing towards said light receiving elements said reflected light from the eye fundus that has been separated from the incident laser beam and deflected one-dimensionally in a direction parallel to said detection slit.

8. An ophthalmic examination apparatus according to claim 7, wherein said first optical deflector is an acousto-optical device.

9. An ophthalmic examination apparatus according to claim 7, wherein said second optical deflector is an oscillating mirror.

10. An ophthalmic examination apparatus according to claim 7, wherein a range of laser beam deflection angles can be varied to vary an angle of view of an eye fundus being examined independently of a deflection angle of said first optical deflector.

11. An ophthalmic examination apparatus according to claim 10, wherein the range of angles of laser beam deflection produced by the second optical deflector can be varied in accordance with the variation in said laser beam deflection angle.

12. An ophthalmic examination apparatus in which a laser beam is deflected at an eye fundus under examination to scan said eye fundus two-dimensionally, and light reflected back from said eye fundus is detected for photoelectric conversion to obtain information about the eye fundus, said apparatus comprising:

a laser light source for producing said laser beam of a single or plurality of wavelength;

a first non-mechanical optical deflector for deflecting said laser beam to scan said eye fundus in one direction at a predetermined frequency;

an optical system capable of changing the range of angles of deflection of said one-dimensionally deflected laser beam independently of the angle of deflection of said first optical deflector;

a second mechanical optical deflector for deflecting said laser beam to scan said eye fundus in a direction perpendicular to the scanning direction of said first optical deflector at a frequency that is lower than the frequency of said first optical deflector; and a electronic control means for varying the range of the angles of deflection of said laser beam deflected by said second optical deflector, so that the range of angles of view of said eye fundus can be varied.

13. An ophthalmic examination apparatus according to claim 12, wherein said first optical deflector is an acousto-optical device.

14. An ophthalmic examination apparatus according to claim 12, wherein said second optical deflector is an oscillating mirror.

15. An ophthalmic examination apparatus according to claim 12, wherein variation of the angle of view of said eye fundus is effected by changing the focal point of an angle-of-view change lens disposed in said optical system.

16. An ophthalmic examination apparatus according to claim 15, wherein adjacent to said angle-of-view change lens is disposed a diopter adjustment lens the focal point of which can be adjusted with respect to said eye fundus.

17. An ophthalmic examination apparatus according to claim 15, wherein said angle-of-view change lens and said diopter adjustment lens are disposed away from the optical path of the reflected light from said eye fundus.

18. An ophthalmic examination apparatus according to claim 15, wherein the range of variation in the angles of deflection of the laser beam deflected by the second optical deflector is varied in accordance with changes in the focal point of the angle-of-view change lens.

* * * * *